United States Patent [19]

Hoeschele et al.

[11] 4,234,499

[45] Nov. 18, 1980

[54] CIS-DIAMMIREPLATINUM(II) ORGANOPHOSPHATE COMPLEXES

[75] Inventors: James D. Hoeschele, Oak Ridge, Tenn.; Alan R. Amundsen, Somerville, N.J.

[73] Assignee: Engelhard Minerals & Chemicals Corporation, Iselin, N.J.

[21] Appl. No.: 17,992

[22] Filed: Mar. 7, 1979

[51] Int. Cl.³ .............................................. C07F 15/00
[52] U.S. Cl. .............................. 260/429 R; 536/117; 424/287
[58] Field of Search ..................... 536/117; 260/429 R

[56] References Cited

U.S. PATENT DOCUMENTS 3,759,896  9/1973  Komatsu et al. ................ 536/117 X

OTHER PUBLICATIONS

Cleare, "Transition Metal Complexes in Cancer Chemotherapy", Coordination Chemistry Rev. 12 pp. 349–405 (1974).

Cleare et al., Bioinorganic Chemistry 2 pp. 187–210 (1973).

Gale et al., Cancer Treatment Reports 61 pp. 1519–1525 (1977).

Connors et al., Platinum Coordination Complexes in Cancer Chemotherapy, Springer-Verlag, N.Y., pp. 63 to 72 (1973).

*Primary Examiner*—Helen M. S. Sneed

[57] ABSTRACT

Cis-diammineplatinum(II) organophosphate complexes where the organophosphate moiety is a glycerophosphate or a monosaccharide phosphate moiety are prepared by reaction of cis-diaquodiammineplatinum(II) salts with alkali metal organophosphates. The resulting complexes possess pronounced anti-tumor activity in mice and low toxicity; consequently, they have high therapeutic indices.

10 Claims, 1 Drawing Figure

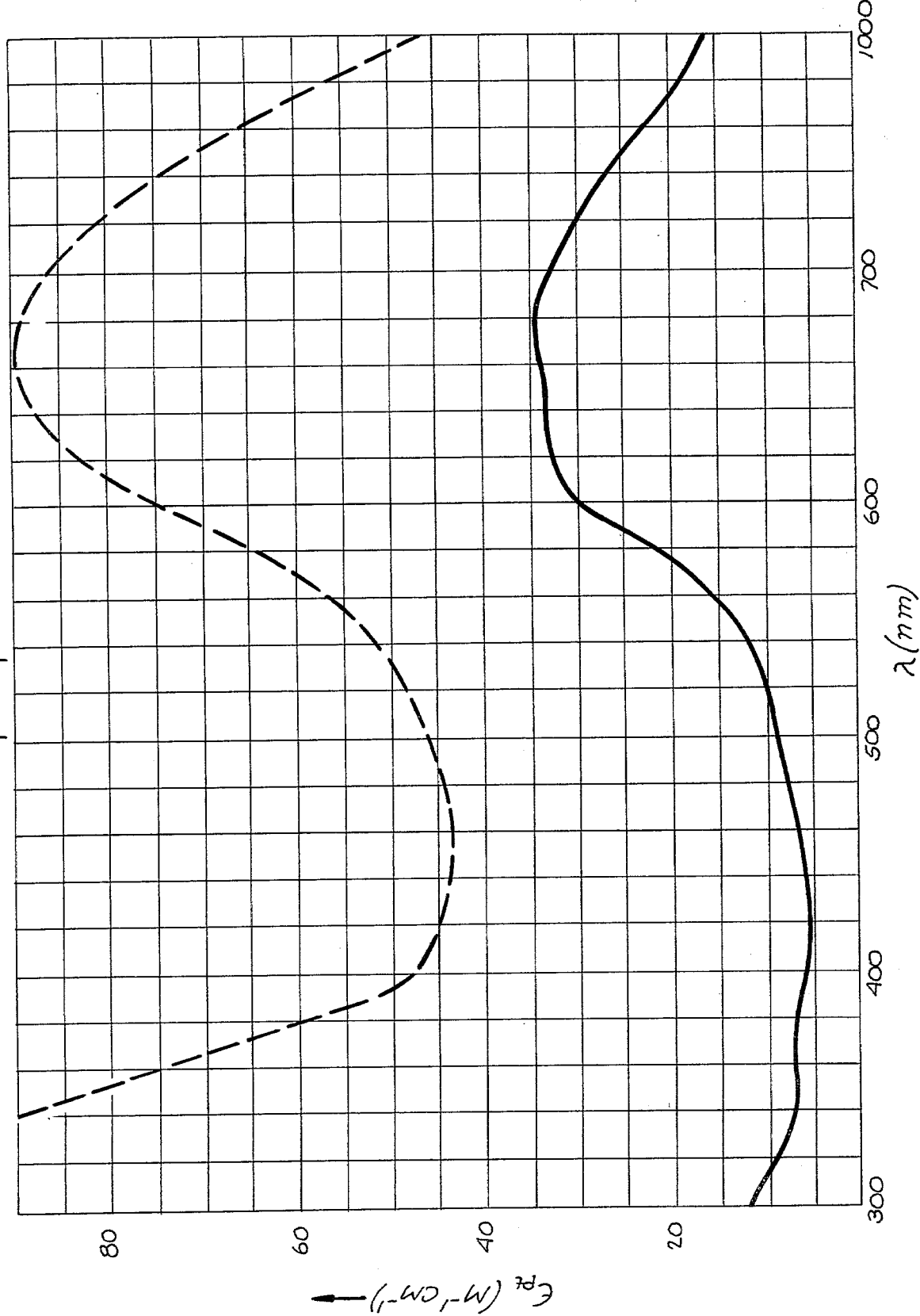

CIS-DIAMMIREPLATINUM(II) ORGANOPHOSPHATE COMPLEXES

This invention is concerned with cis-diammineplatinum(II) organophosphate complexes. More particularly, this invention is concerned with cis-diammineplatinum(II) organophosphate complexes, where the organophosphate moiety is either a glycerophosphate or a monosaccharide phosphate. These complexes are characterized by pronounced activity against tumors in mice combined with low animal toxicity.

BRIEF SUMMARY OF THE DRAWINGS

FIG. 1 shows the electronic spectra of the complexes of Examples 1 and 3.

BACKGROUND

Rosenberg, et al reported the discovery that certain platinum coordination compounds are of interest as potential anti-tumor agents (Rosenberg et al, "Platinum Compounds: A New Class of Potent Anti-Tumor Agents," Nature, Vol. 222 (Apr. 26, 1969), pp. 385–86.) Since then, considerable effort has been expended to evaluate various classes of coordination complexes for similar activity. See, e.g. M. J. Cleare, "Transition Metal Complexes in Cancer Chemotherapy," Coordination Chemistry Reviews, 12 (1974), pp. 349–405. Cis-diammineplatinum pyrophosphate complexes of the empirical formula $\{Pt(NH_3)_2\}_2P_2O_7$ have been reported; however, they have only marginal activity. (Cleare et al, "Studies of the Antitumor Activity of Group VIII Transition Metal Complexes," Part I, Platinum(II) Complexes, Bioinorganic Chemistry, 2, pp. 187–210 (1973) at p. 199.)

Recently, a non-blue, relatively insoluble, glycerophosphate complex of 1,2-diaminocyclohexaneplatinum(II), containing 39.12% platinum (Pt), was reported to show anti-tumor activity (G. R. Gale et al, "Preparation and Anti-Tumor Evaluation of Water-Soluble Derivatives of Dichloro-1,2-diaminocyclohexane platinum(II)", Cancer Treatment Reports, 61, pp. 1519–1525 (1977)).

SUMMARY OF THE INVENTION

In accordance with the present invention, there is provided a novel class of cis-diammineplatinum(II) organophosphate complexes, where the organophosphate moiety is either a glycerophosphate or a monosaccharide phosphate, which show pronounced anti-tumor activity in mice combined with the exhibition of low toxicity in mammals. As a consequence, the complexes of this invention have a favorable therapeutic index.

The complexes of this invention may be designated by the general formula $[Pt(NH_3)_2(R^1(OPO_3)_z)_y]$, wherein $(R^1(OPO_3)_z)$ is the organophosphate moiety as hereinafter defined and y is about 0.4 to 0.9.

The organophosphate moiety of the complexes of this invention may be represented by the general formula $(R^1(OPO_3)_z)$ wherein z is 1 or 2 and wherein $R^1$ is a monovalent residue of glycerol or a monovalent or divalent residue of a monosaccharide. That residue is formed by removal of one or two of the hydroxyls of said glycerol or monosaccharide. Illustrative organophosphate moieties include the α-D,L-glycerophosphate, β-glycerophosphate, α-D-glucose-1-phosphate, D-glucose-6-phosphate, D-fructose-6-phosphate, D-galactose-6-phosphate, D-ribose-5-phosphate, and D-fructose-1,6-diphosphate moieties.

The remainder of the organophosphate platinum(II) complex comprises a $Pt(II)(NH_3)_2$ moiety.

The complexes of this invention are prepared by reacting a diaquodiammineplatinum(II) salt with an organophosphate salt in an aqueous medium.

The diaquodiammineplatinum(II) salt is represented by the formula:

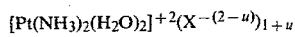

wherein X is an inorganic anion and u is 0 or 1. Suitable anions are those which are stable in acid media which do not affect pH; they include sulfate, nitrate, and perchlorate, although nitrate is preferred. Anions having a greater complexing activity than water or organophosphate, such as chloride, iodide and bromide are not suitable.

The diaquo salt is formed by the stoichiometric reaction of cis-dichlorodiammineplatinum(II) with a silver salt, preferably silver nitrate, in an aqueous medium at room temperature. The diaquo salt is unstable in solution, but may be converted to stable solid cis-$[Pt(NH_3)_2(OH)]_2(X)_2$ by reaction with one gram mole of base per gram atom of platinum. This dimeric complex may be reconverted to monomer with acid or used directly in the preparation of phosphate compounds.

The organophosphate salts which are employed are preferably alkali metal and alkaline earth metal organophosphate salts, such as those represented by general formula $M_w(R^1(OPO_3)_z)$ wherein $R^1(OPO_3)_z$ is defined as previously and wherein M is an alkali metal or alkaline earth metal ion, and w is 1,2 or 3. Illustrative salts include disodium α-D,L-glycerophosphate, disodium α-D-glucose-1-phosphate and barium D-ribose-5-phosphate.

The organophosphate complexes of this invention are formed by contacting approximately equimolar portions of the diaquoplatinum(II) salt in aqueous media with an organophosphate salt. The reaction mixture is desirably agitated, as by stirring or shaking. The reaction proceeds according to the following equation:

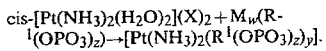

High concentrations of reactants, that is in the range of approximately 0.3 M to 0.7 M, favor formation of the complex. The reaction medium is acidic, and preferably has a pH between about 5 to about 6. The reaction normally is carried out at ambient temperatures, although higher and lower temperatures, e.g. from about 20° C. to about 40° C., may be employed. The reaction time required may vary from about 30 days to about 90 days or even longer.

Depending on the organophosphate moiety, the complexes of this invention may be either water-soluble or water-insoluble.

Thus, water-soluble complexes result from employing organophosphates such as α-and β-glycerophosphates, α-D-glucose-1-phosphate and D-glucose-6-phosphate. They appear to have the cis-$[Pt(NH_3)_2]$ unit intact, wherein the two amine moieties are in a cis-configuration to the square planar platinum; and have phosphorous/platinum ratios which range from about 0.7 to about 0.9. These complexes are believed to be polymeric.

The water-insoluble complexes result when organophosphates such as D-fructose-6-phosphate, D-galactose-6-phosphate and D-ribose-5-phosphate are employed. They have low phorphorous to platinum ratios, of the order of from 0.4 to 0.5, as well as low nitrogen to platinum ratios, of the order of from 1.4 to 1.6. The low nitrogen to platinum ratios are believed to indicate that the cis-Pt(NH$_3$)$_2$ units are disrupted in those complexes.

The complexes of this invention are especially useful in tumor chemotherapy, having been found active against sarcoma 180 ascites in mice. The complexes are administered intraperitoneally as an aqueous solution in a generally known manner or, in cases where a complex has low solubility in water, in a slurry with Klucel (hydroxypropyl cellulose) or other suitable suspending agent. The solution or slurry may contain other components, such as physiologically acceptable salts, other medicaments, etc. The dosage is not narrowly critical, and indeed it is a feature of the complexes of this invention that, because of their relatively low toxicity, they may be administered over a wide dosage range, from about 10 mg/kg to about 200 mg/kg. However, the optimum dosage level may vary between the different complexes.

The following examples are illustrative:

EXAMPLE 1

Synthesis of Cis-diammineplatinum(II)
α-D,L-glycerophosphate Complex

To 33 ml of 0.3 M cis-[Pt(NH$_3$)$_2$(H$_2$O)$_2$](NO$_3$)$_2$ solution, 2.16 grams of disodium α-D,L-glycerophosphate was added. The mixture was stoppered by a porous plug and then stirred in air for 42 days, with periodic additions of water to maintain its volume at 40 ml. During the time it was being stirred, the solution became blue in color. After the addition of 60 ml of ethanol to the solution and storage of the mixture in a freezer overnight, a blue glassy material separated out of the solution. The supernatant was decanted, the precipitate washed with cold 1:1 water: ethanol, and redissolved in 1 ml water. Then 3 ml of ethanol were added and the mixture was stored in the freezer again to precipitate the complex. The complex was washed, dissolved and precipitated again. The final residue was dissolved in 1 ml water and then dried, in vacuum, yielding 0.4398 grams of the above-identified complex.

Elemental analysis of the complex gave the following results:

|  | %C | %H | %N | %P | %Pt | N/Pt | P/Pt |
|---|---|---|---|---|---|---|---|
| (original) | 8.23 | 3.21 | 7.02 | 6.98 | 47.04 | 2.08 | 0.93 |
| (repeat) | 6.36 | 3.39 | 7.74 | 6.74 | 50.82 | 2.12 | 0.83 |
| (average) | 7.30 | 3.30 | 7.38 | 6.86 | 48.93 | 2.10 | 0.88 |

Infrared spectral data for this complex appear in Table I along with tentative band assignments. Small differences in the phosphate, Pt-N and Pt-O regions are observed between different preparations of the same complex.

TABLE I

Infrared Spectral Data[a]
Cis-diammineplatinum(II) α-D-L-glycerophosphate

| Absorption Band | Assignment |
|---|---|
| 3000–3500 broad | νNH, νOH |
| 1550–1700 broad | δNH$_3$, δH$_2$O |

TABLE I-continued

Infrared Spectral Data[a]
Cis-diammineplatinum(II) α-D-L-glycerophosphate

| Absorption Band | Assignment |
|---|---|
| 1130 | |
| 1070 | |
| 1030 | νPO |
| 960 sh | νC—O |
| 930 | ρNH$_3$ |
| 860 | |
| 830 sh | |
| 595 | νPt—O |
| 555 | |
| 510 | νPt—N |

[a]Wavenumbers in cm$^{-1}$, sh = shoulder

The electronic spectrum for the complex is reproduced in FIG. 1. Molar absorptivities (M$^{-1}$ cm$^{-1}$) are given in terms of Pt, based on Pt analysis. Dissolution of the complex in water at a concentration of 0.8 mg/ml gave an intensely blue solution with λ max at 685 nm (shoulder 635 nm).

EXAMPLE 2

Synthesis of Cis-diammineplatinum(II)
α-glycerophosphate Complex

A 15.05-gram portion of disodium β-glycerophosphate was dissolved in 100 ml of 0.5 M cis-[Pt(NH$_3$)$_2$(H$_2$O)$_2$](NO$_3$)$_2$ to give a solution with an initial pH of 5.5 and a total volume of 150 ml. The solution was stoppered with a porous plug and stirred in air and at room temperature for 60 days. The above-identified complex was isolated by the same precipitation and a washing method as described in Example 1.

Elemental analysis gave the following results: C, 8.49%; H, 3.53%; N, 7.60%; P, 6.51%; Pt, 52.42%. The N/Pt ratio was found to be 2.01 and the P/Pt ratio was 0.78.

EXAMPLE 3

Synthesis of Cis-diammineplatinum(II)
α-D-glucose-1-phosphate Complex

A 3.76-gram portion of disodium α-D-glucose-1-phosphate was dissolved in 33.3 ml of a 0.3 M solution of cis-[Pt(NH$_3$)$_2$-(H$_2$O)$_2$](NO$_3$)$_2$. The resulting solution had an initial pH of 5.2. The solution was stoppered with a porous plug and then stirred for 90 days at room temperature, turning deep blue in color. During that period, water was periodically added to maintain the solution volume at 40 ml. At the end of the three month period, 60 ml of ethanol were added to the solution and a dark blue material was precipitated by placing the mixture in a freezer overnight. The supernatant was decanted, and the precipitate was washed with 70% ethanol, and then it was redissolved in 40 ml of water. The solution was filtered; and the blue material was reprecipitated by the addition of 50 ml ethanol to the solution. After overnight storage in a freezer, additional decanting, washing, and drying by the procedures described in Example 1, there were obtained 2.548 grams of the above-identified complex as a dark blue solid.

Elemental analysis gave the following results:

|  | %C | %H | %N | %P | %Pt | N/Pt | P/Pt |
|---|---|---|---|---|---|---|---|
| (original) | 12.65 | 3.57 | 6.06 | 5.37 | 42.50 | 1.98 | 0.79 |
| (repeat) | 12.09 | 4.24 | 6.03 | 4.31 | 42.55 | 1.97 | 0.64 |

| | %C | %H | %N | %P | %Pt | N/Pt | P/Pt |
|---|---|---|---|---|---|---|---|
| (average) | 12.37 | 3.90 | 6.04 | 4.84 | 42.52 | 1.98 | 0.72 |

Infrared spectra data for this product, along with tentative band assignments, appear in Table II. Small differences in the phosphate, Pt-N, and Pt-O regions were observed between different preparations of the complex.

TABLE II

Infrared Spectral Data[a]
Cis-diammineplatinum(II) α-D-glucose-1-phosphate Complex

| Absorption Band | Assignment |
|---|---|
| 3000–3500 broad | $\nu$NH, $\nu$OH |
| 1500–1700 broad | $\delta$NH$_3$, $\delta$H$_2$O |
| 1130, 1070, 1040, 930, 860, 830 sh | $\nu$PO, $\nu$C—O, $\rho$NH$_3$ |
| 580, 565, 510, 485 | $\nu$Pt—O, $\nu$Pt-N |

[a]Wavenumbers in cm$^{-1}$, sh = shoulder

An electronic spectrum of the complex of Example 3 is included in FIG. 1. Molar absorptivities (M$^{-1}$cm$^{-1}$) are given in terms of Pt, based on Pt analysis. The product of Example 3, in a 2 mg/ml aqueous solution, gave an intensely blue solution with λ max at 680 nm.

EXAMPLE 4

Synthesis of Cis-diammineplatinum(II) D-glucose-6-phosphate Complex

To 22.5 ml of a 0.67 M aqueous solution of cis-[Pt(NH$_3$)$_2$-(H$_2$O)](NO$_3$)$_2$, the pH of which had been adjusted to 4 with sodium hydroxide, there was added 4.23 grams disodium D-glucose-6-phosphate dissolved in 30 ml of water. The pH of the reaction mixture was then adjusted to 5.0 using 2 M nitric acid. The solution was stoppered, and stirred for 42 days as in the previous examples. The above-identified, water-soluble blue complex was isolated by the method described in Example 1 in a yield of 2.69 grams.

Elemental analysis of the product gave the following results: C, 12.64%; H, 3.63%; N, 6.27%; P, 5.50%; Pt, 42.70%. The N/Pt and P/Pt ratios of the above-identified complex were found to be 2.05 and 0.81 respectively.

EXAMPLE 5

Synthesis of Cis-diammineplatinum(II) D-fructose-6-phosphate Complex

To 18.5 ml of 0.67 M cis-[Pt(NH$_3$)$_2$(H$_2$O)$_2$](NO$_3$)$_2$, 4.5 grams of disodium D-fructose-6-phosphate were added. The solution was stoppered with a porous plug and stirred for 49 days. At the end of that time, a blue, water-insoluble precipitate had formed. It was collected, and then washed by alternate centrifugation and resuspension. The precipitate was vacuum dried to yield 3.6 grams of the above-identified complex.

Elemental analysis gave the following results: C, 8.96%; H, 2.55%; N, 6.12%; P, 4.00%; Pt,60.98%. The N/Pt ratio was found to be 1.40. The P/Pt ratio was 0.41.

EXAMPLE 6

Synthesis of Cis-diammineplatinum(II) D-galactose-6-phosphate Complex

The pH of an 11.3-ml aqueous solution of 0.67M cis-[Pt(NH$_3$)$_2$(H$_2$O)$_2$](NO$_3$)$_2$ was adjusted with sodium hydroxide to 4. Then, 3.0 grams of barium D-galactose-6-phosphate dissolved in 30 ml water were added. The pH of the resulting solution was adjusted to 5.0 with 2 M nitric acid. After stoppering the solution with a porous plug and stirring for 21 days, the above-identified complex which had formed during that time period was recovered as a water-insoluble blue precipitate by the method described in Example 5.

Elemental analysis gave the following results: C, 8.75%; H, 2.54%; N, 5.76%; P, 4.22%; Pt, 59.95%. The N/Pt ratio of the complex was 1.34. Its P/Pt ratio was found to be 0.44.

EXAMPLE 7

Synthesis of Cis-diammineplatinum(II) D-ribose-5-phosphate Complex

This complex was made by adding 1.0 grams of barium D-ribose-5-phosphate to 4.08 ml of 0.67 M cis-[Pt(NH$_3$)$_2$(H$_2$O)$_2$](NO$_3$)$_2$. The reaction flask was stoppered with a porous plug, and the reaction mixture was stirred for 35 days. After that time, the water-insoluble blue-black product which had formed was isolated and washed by the method described in Example 5, yielding 0.275 grams of the above-identified complex.

Elemental analysis gave the following results: C, 8.82%; H, 2.53%; N, 5.73%; P, 4.47%; Pt, 60.02%. The N/Pt ratio of the complex was found to be 1.33; its P/Pt ratio was 0.47.

EXAMPLE 8

Synthesis of Cis-diammineplatinum(II) D-fructose-1,6-diphosphate Complex

A 5.0 gram portion of trisodium D-fructose-1,6-diphosphate was dissolved in 10 ml water. The resulting solution was added to 14.1 ml of a 0.67 M aqueous solution of cis-[Pt(NH$_3$)$_2$(H$_2$O)$_2$](NO$_3$)$_2$. The reaction mixture was allowed to stand for 28 days in a 40° C. bath. After that time, the dark blue water-insoluble precipitate which had formed was filtered, washed with water and ethanol, and then dried in vacuum, to yield 0.566 grams of the above-identified complex.

Elemental analysis gave the following results: C, 7.46%; H, 2.85%; N, 6.26%; P, 7.79%; Pt, 55.67%. The N/Pt ratio was found to be 1.57. The P/Pt ratio of the complex was 0.88.

EXAMPLE 9

Evaluation of the Anti-Tumor Activity of the Complexes of Examples 1-8 in the Mouse S180a Tumor System The cis-diammineplatinum(II) organophosphate complexes of Examples 1 through 8 were tested for anti-tumor activity against S180 ascites in female Swiss white mice by the following procedure:

CFW mice, averaging 20 grams, were immediately inspected, weighed, and then placed in newly prepared cages (6 mice/cage or 1 set). On day 0, the mice were inoculated with 0.2 ml of a freshly prepared saline suspension (0.15 M NaCl) containing 1×10$^7$ tumor cells/ml or a total of 2×10$^6$ cells. This inoculum was freshly prepared using "transfer" mice which had been injected with tumor cells the previous week, and was the end-product of a series of steps which involved (1) the removal of the cells from the peritoneal cavity of the sacrificed transfer mouse, (2) alternate centrifugation-washing (2–3 times with cold saline) to remove occasional blood and other undesirable components, and (3) dilution (1:3) of the packed cell volume with saline (the final centrifugation being carried out at 1000 rpm for two minutes). A cell count was made (in duplicate) on a 100-fold dilution of this 1:3 suspension (nominally $5 \times 10^7$ cells/ml) by means of a hemacytometer counting chamber and a microscope and in most cases by means of a Coulter Counter. A final dilution to $1 \times 10^7$ cells/ml was based on the averaged count (normally 500–600 cells were counted to obtain reliable statistics when the hemacytometer method was employed). On day 1, mixtures of the test compounds were prepared and the mice injected with each mouse of a set of six mice being injected with the same test compound at the same dosage level. The doses were based on the average weight of the animals (cage weights).

Also, on day 1 two types of controls were employed: (1) Normal (1 set): 0.5 ml of the carrier used for the test compound; and (2) Positive Control (1 set): cis-dichlorodiammineplatinum(II), a known anti-tumor agent, used at 7 or 8 mg/kg as a check on the response of the biological test system.

The effectiveness of a compound was measured in terms of the % increase in life span (%ILS) of the test animals relative to the normal controls (calculated from the day of tumor inoculation (day 0)). In order to standardize the test data and permit intercomparisons to be made, the day of evaluation was arbitrarily taken as that day corresponding to twice the mean life span (or average day of death) of the normal controls. This set a practical upper limit of 100% on the %ILS attainable. For purposes of calculation, survivors on the day of evaluation were considered to have died on that day. The %ILS was formulated as:

$$\%ILS = \left( \frac{\text{mean life-span of test mice}}{\text{mean life-span of control mice}} - 1 \right) \times 100$$

ILS values in excess of 50% indicate significant anti-tumor activity, while values in excess of 75% indicate high activity.

The water-soluble complexes of Examples 1–4 were tested either in solution in water or in 0.05 M aqueous solutions of the disodium salt of the organophosphate involved. The water-insoluble complexes of Examples 5–8 were tested as slurries in water containing the suspending agent Klucel (0.1–0.3% Klucel used).

The results of the anti-tumor screening tests using the sarcoma 180 ascites (S180a) system in mice appear in Table III.

TABLE III

Anti-Tumor Screening Data for the Complex of Examples 1–8 Obtained on the S180a Tumor System

| Complex of Example # | Carrier | Test Compound | | | Positive Control | |
|---|---|---|---|---|---|---|
| | | Dose[a] (mg/kg) | %ILS | 30-Day Survivors | %ILS[b] | 30-Day Survivors |
| 1 | H₂O | 20 | 45 | 2 | 97(7) | 1 |
| | | 40 | 100 | 3 | | |
| | | 80 | 100 | 5 | | |
| | | 160 | −4 | 2 | | |
| 1 | H₂O | 20 | 81 | 4 | 79(7) | 2 |
| | | 40 | 100 | 6 | | |
| | | 80 | 96 | 5 | | |
| | | 160 | 77 | 3 | | |
| 1[c] | H₂O | 20 | 95 | 2 | 68(8) | 2 |
| | | 40 | 94 | 3 | | |
| | | 80 | −22 | 1 | | |
| | | 160 | −53 | 0 | | |
| 2 | H₂O | 20 | 90 | 3 | 51(8) | 0 |
| | | 40 | 95 | 5 | | |
| | | 80 | 91 | 5 | | |
| | | 160 | 10 | 0 | | |
| 3 | 0.05M Na₂(α-D-glucose-1-phosphate) | 20 | 10 | 0 | 72(7) | 0 |
| | | 40 | 32 | 0 | | |
| | | 80 | 55 | 2 | | |
| | | 160 | 63 | 4 | | |
| | | 320 | −79 | 0 | | |
| 3[c] | H₂O | 20 | 38 | 0 | 68(8) | 2 |
| | | 40 | 97 | 3 | | |
| | | 80 | 89 | 3 | | |
| | | 160 | 42 | 1 | | |
| 4 | H₂O | 40 | 94 | 5 | 32(8) | 0 |
| | | 80 | 62 | 3 | | |
| | | 160 | −7 | 2 | | |
| | | 320 | −88 | 0 | | |
| 5 | Klucel/H₂O Slurry | 25 | 94 | 5 | 42(8) | 0 |
| | | 50 | 50 | 4 | | |
| | | 100 | −79 | 0 | | |
| | | 150 | −88 | 0 | | |
| 6 | Klucel/H₂O Slurry | 25 | 82 | 4 | 42(8) | 0 |
| | | 50 | 43 | 4 | | |
| | | 100 | −88 | 0 | | |
| | | 150 | −84 | 0 | | |
| 7 | Klucel/ | 10 | 57 | 0 | 89(8) | 3 |

TABLE III-continued

Anti-Tumor Screening Data for the Complex of Examples 1-8 Obtained on the S180a Tumor System

| Complex of Example # | Carrier | Test Compound | | | Positive Control | |
|---|---|---|---|---|---|---|
| | | Dose[a] (mg/kg) | %ILS | 30-Day Survivors | %ILS[b] | 30-Day Survivors |
| | $H_2O$ | 20 | 100 | 6 | | |
| | Slurry | 40 | 100 | 6 | | |
| | | 80 | −98 | 0 | | |
| 8 | $H_2O$ | 20 | 86 | 4 | 71(8) | 2 |
| | Slurry | 40 | 77 | 4 | | |
| | | 80 | −44 | 1 | | |
| | | 160 | −70 | 0 | | |

[a]6 mice/dose unless otherwise indicated.
[b]Positive control = 7 or 8 mg/kg cis-[Pt(NH_3)_2Cl_2] in saline.
[c]4 mice/dose The water-soluble complexes of Examples 1-4, varied with respect to their most active range. The α-D,L-glycerophosphate complex of Example 1 was most active in the 40-80 mg/kg range; the β-glycerophosphate complex of Example 2 was most active in the 20-80 mg/kg range; the αD-glucose-1-phosphate complex of Example 3 was most active in the 40-160 mg/kg range; and the D-glucose-6-phosphate complex of Example 4 was most active in the 40-80 mg/kg range. The toxic dose for Examples 1-4 was quite high. It was 160 mg/kg for Example 1 and 320 mg/kg for Examples 3 and 4, while the toxic dose for the complex of Example 2 was not reached. The screening results for repeat preparations of the complexes of Examples 1 and 3 demonstrate consistency in anti-tumor activity despite some variations in analysis.

In the case of the water-insoluble organophosphates, both activity and toxicity appeared at slightly lower absolute doses. However, the therapeutic indices of the two groups (water-soluble and water-insoluble) appeared to be similar. The D-fructose-6-phosphate complex of Example 5 and the D-galactose-6-phosphate complex of Example 6 were most active at dosages of 25 mg/kg and were toxic at dosages of 100 mg/kg. The D-ribose-5-phosphate complex of Example 7 was most active in the range of about 20 to about 40 mg/kg; toxicity appeared at a dose of 80 mg/kg. The D-fructose-1,6-diphosphate complex of Example 8 was most active in the 20-40 mg/kg range and was toxic at dose of 80 mg/kg.

EXAMPLE 10

Evaluation of the Anti-Tumor Activity of the Complexes of this Invention in the Mouse L1210 and P388 Systems The complexes of this invention were also screened for activity against the lymphoid leukemia L1210 and lymphocytic leukemia P388 systems in mice, in which the mean survival time as compared with control mice (T/C) was determined. The T/C* was calculated as follows:

*T/C is related to %ILS by the relationship T/C-100=%ILS $$T/C = \left( \frac{\text{mean life-span (Test)}}{\text{mean life-span (Control)}} \right) \times 100$$

T/C values of 125 or greater represent significant activity. The data from these tests are summarized in Table IV.

TABLE IV

Anti-Tumor Screening Results vs the L1210 and P388 Tumor Systems

| Complex of Example # | Tumor System | Dose[a] Regimen | Dose (mg/kg) | T/C | Survivors[b] |
|---|---|---|---|---|---|
| 1 | L1210 | Day 1,5,9 | 200 | T[c] | 0/6 |
| | | | 100 | T | 0/6 |
| | | | 50 | T | 6/6 |
| | | | 25 | 141 | 6/6 |
| | | | 12.5 | 134 | 6/6 |
| 1 | P 388 | Day 1-9 | 6.25 | T | 6/6 |
| | | | 3.12 | 209 | 6/6 |
| | | | 1.56 | 187 | 6/6 |
| | | | 0.78 | 126 | 6/6 |
| 3 | L1210 | Day 1-9 | 200 | T | 0/6 |
| | | | 100 | T | 0/6 |
| | | | 50 | T | 0/6 |
| | | | 25 | T | 6/6 |
| | | | 12.5 | 160 | 6/6 |
| 3 | P 388 | Day 1-9 | 50 | T | 2/6 |
| | | | 25 | T | 4/6 |
| | | | 12.5 | T | 6/6 |
| | | | 6.25 | 155 | 6/6 |
| | | | 3.13 | 141 | 6/6 |

[a]Day 1-9 = Daily dose, day 1 through 9
Day 1, 5, 9 - Doses administered on days 1, 5 and 9
[b]Number of survivors on day 5
[c]T = Toxic by NCI definition (See Geran et al, Cancer Chemo. Rep., Pt. 3, Summer 1972).

Based on the data set forth in Table IV, the α-D,L-glycerophosphate complex of Example 1 was highly active against P388 on a schedule of 9 daily doses, with maximum activity observed at a dose of 3.12 mg/kg. This complex was also active against L1210, but less markedly so. The α-D-glucose-1-phosphate complex of Example 3 was also active against P388 when given on a regimen of 9 daily doses, with peak activity occurring at a dose of 6.25 mg/kg. This complex was active against L1210 when given on a 9 daily dose regimen.

What is claimed is:

1. A platinum(II) organophosphate complex of the formula:

[Pt(NH_3)_2(R^1(OPO_3)_z)_y]

in which $R^1(OPO_3)_z$ is an organophosphate moiety where $R^1$ is selected from the group consisting of the monovalent residue of glycerol and the monovalent and divalent residues of a monosaccharide, and y is an integer having a value of from about 0.4–0.9 and z is 1 or 2.

2. A complex according to claim 1 wherein the organophosphate moiety is selected from the group consisting of α-D,L-glycerophosphate, β-glycerophosphate, α-D-glucose-1-phosphate, D-glucose-6-phosphate, D-fructose-6-phosphate, D-galactose-6-phosphate, D-ribose-5-phosphate, and D-fructose-1,6-diphosphate.

3. A complex according to claim 1 wherein said organophosphate moiety is α-D,L-glycerophosphate.

4. A complex according to claim 1 wherein said organophosphate moiety is β-glycerophosphate.

5. A complex according to claim 1 wherein said organophosphate moeity is α-D-glucose-1-phosphate.

6. A complex according to claim 1 wherein said organophosphate moeity is D-glucose-6-phosphate.

7. A complex according to claim 1 wherein said organophosphate moeity is D-fructose-6-phosphate.

8. A complex according to claim 1 wherein said oganophosphate moeity is D-galactose-6-phosphate.

9. A complex according to claim 1 wherein said organophosphate moeity is D-ribose-5-phosphate.

10. A complex according to claim 1 wherein said organophosphate is D-fructose-1,6-diphosphate.

* * * * *